United States Patent [19]

Tung et al.

[11] Patent Number: 4,937,398
[45] Date of Patent: Jun. 26, 1990

[54] PROCESS FOR THE PREPARATION OF FLUORINATED ALKANES FROM ALKENES

[75] Inventors: Hsueh S. Tung, Williamsville; Richard E. Eibeck, Orchard Park; Bernard Sukornick, Williamsville, all of N.Y.

[73] Assignee: Allied-Signal Inc., Morris Township, Morris County, N.J.

[21] Appl. No.: 290,129

[22] Filed: Dec. 27, 1988

[51] Int. Cl.$^5$ .................. C07C 17/02; C07C 17/04; C07C 19/02; C07C 17/06
[52] U.S. Cl. ........................ 570/175; 570/134; 570/172
[58] Field of Search ............................. 570/175

[56] References Cited

U.S. PATENT DOCUMENTS

| | | | |
|---|---|---|---|
| 1,996,115 | 4/1935 | Lazier | 570/175 |
| 2,830,101 | 4/1950 | Swamer | 570/175 |
| 3,215,748 | 11/1965 | Baranauckas et al. | 570/175 |
| 3,862,995 | 1/1975 | Martens et al. | 570/175 |
| 4,684,452 | 8/1987 | Marchionni et al. | 204/157 |
| 4,754,085 | 6/1988 | Gervasutti et al. | 570/175 |
| 4,792,643 | 12/1988 | Sobolev | 570/168 |

OTHER PUBLICATIONS

R. Merritt "Direct Fluorination of 1,1-Diphenylethylene", J. Org. Chem. 31, 3871 (1966).
N. Watanabe et al., "Some Properties of Fluorine-Adsorbed Active Carbon", Bull Chem. Soc. Jpn. 54, 127 (1981).

*Primary Examiner*—J. E. Evans
*Attorney, Agent, or Firm*—Melanie L. Brown; Jay P. Friedenson

[57] ABSTRACT

The present invention provides a process for the preparation of luorinated alkanes. The process comprises the step of: reacting an alkene with carbon having fluorine absorbed therein at a temperature and for a time sufficient to form fluorinated alkanes. The alkene used is not perhalogenated at the double-bonded carbons. Preferably, the alkene used is vinylidene fluoride or ethylene.

The process produces products such as 1,1,1,2-tetrafluoroethane (known in the art as 134a) which may be used as a refrigerant and 1,1,1-trifluoroethane (known in the art as R143a) and 1,2-difluoroethane (known in the art as R152) which may be used as blowing agents or solvents.

14 Claims, No Drawings

PROCESS FOR THE PREPARATION OF FLUORINATED ALKANES FROM ALKENES

BACKGROUND OF THE INVENTION

The present invention relates to a process for the preparation of fluorinated alkanes from alkenes, and more particularly, to a process for the preparation of fluorinated alkanes such as 1,1,1,2-tetrafluoroethane (known in the art as R134a).

R134a has been mentioned as a possible replacement for dichlorodifluoromethane (known in the art as R12) because concern over potential depletion of the ozone layer exists. R12 is used in closed loop refrigeration systems; many of these systems are automotive air-conditioning systems. R134a has properties similar to those of R12 so that it is possible to substitute R134a for R12 with minimal changes in equipment being required. Currently, R134a is unavailable in commercial quantities; therefore, a need exists for a commercially viable process for the preparation of R134a.

Other refrigerants such as 1,1,1-trifluoroethane (known in the art as R143a) are also considered less detrimental to the ozone layer than currently used refrigerants. Currently, R143a is unavailable in commercial quantities; thus, a need also exists for a commercially viable process for the preparation of R143a.

Another refrigerant which is also considered less detrimental to the ozone layer than currently used refrigerants is 1,2-difluoroethane (known in the art as R152). Currently, R152 is also unavailable commercially. Therefore, a need also exists for a commercially viable process for the preparation of R152.

The reaction of organic materials with elemental fluorine has extremely limited utility because fluorine is highly reactive. The fluorination of organic materials with elemental fluorine proceeds spontaneously with explosive rapidity which results in uncontrolled polyfluorination and substrate fragmentation. Because many alkenes are available in commercial quantities, the fluorination of alkenes to produce fluorinated alkanes would be commercially useful. The problem with unsaturated organic materials is that the fluorination reaction is even more violent and dangerous in nature. The fluorination of a double bond evolves large amounts of heat on the order of 107 Kcal per double bond. As a result, breakdown of carbon-carbon sigma bonds occurs and undesired by-products form.

Processes have been designed to eliminate these dangers and drawbacks; unfortunately, these processes suffer from other disadvantages. For example, one approach runs the fluorination at a very low temperature in solvent with a very low concentration of elemental fluorine which is heavily diluted with an inert gas such as nitrogen argon or helium. As a result, this process suffers from an extreme reduction in productivity without alteration of the fluorination mechanism; in other words, regardless of the low fluorine concentration and low temperature, the elemental fluorine still prefers an H abstraction over addition to the double bond.

As an example, Merritt, *J. Org. Chem.* 31, 3871 (1966) reported on the fluorination of 1,1-diphenylethylene at −78° C. in CCl$_3$F using F$_2$. The three products were 1,1-diphenyl-2-fluoroethylene in 78% yield; 1,1-diphenyl-2,2-difluoroethylene in 14% yield, and 1,1-diphenyl-1,2,2-trifluoroethane in 8% yield. As such, the major product was a fluorinated alkene which resulted from hydrogen abstraction while the minor products were fluorinated alkanes which resulted from fluorine addition to the double bond. This process for the preparation of fluorinated alkanes is commercially undesirable because the reaction must be run at a very low temperature. See also U.S. Pat. Nos. 4,684,452 and 4,754,085.

Although another attempted approach used activated carbon having fluorine absorbed therein for the fluorination of perchloroethylene, benzene, and bromobenzene, the results reported by Watanabe et al., *Bull. Chem. Soc. Jpn.* 54, 127 (1981) clearly discourage the use of this approach for the addition of fluorine to alkene. The reference reported that no reaction occurred when the activated carbon having fluorine therein was contacted with benzene at 80° C. or bromobenzene at 100° C. The reference also reported that at 80° C., no reaction occurred when the activated carbon having fluorine absorbed therein was contacted with perchloroethylene; at 250° C., only degraded products such as CF$_4$, CF$_3$Cl, CF$_2$Cl$_2$, and CFCl$_3$ resulted. The presence of these degradation products indicated the rupture of the carbon-carbon sigma bond. Regardless of the temperature used, the results reported in this reference would not lead a person having ordinary skill in the art to use an activated carbon having fluorine absorbed therein for the addition of fluorine to alkenes to form fluorinated alkanes.

As such, a need exists in the art for a commercially viable process for the preparation of fluorinated alkanes, and more particularly, a process for the preparation of R134a, R143a, and R152 wherein the process does not have to be run at low temperatures and a fluorination reaction does indeed occur.

SUMMARY OF THE INVENTION

The present invention fills the need in the art for a process for the preparation of fluorinated alkanes including R134a, R143a, and R152. Proceeding contrary to the teachings of the aforementioned Watanabe et al. article it was unexpectedly discovered that the addition of fluorine to an alkene, which is not perhalogenated at the double-bonded carbons, by the use of carbon having fluorine adsorbed therein proceeds smoothly to yield fluorinated alkanes. The term "not perhalogenated at the double-bonded carbons" is used herein to exclude perchloroethylene as used by Watanabe et al. and any other perhalogenated ethylene or alkene having a —CX═CX$_2$ or —CX═CX— therein wherein X is bromine, chloride, fluorine, or iodine. In contrast to the Merritt process and U.S. Pat. Nos. 4,684,452 and 4,754,085 discussed above wherein the reaction has to be conducted at a very low temperature in solvent the present process allows operation at room temperature and a solvent is not required As such, the present invention provides a process for the preparation of fluorinated alkanes comprising the step of: reacting an alkene with carbon having fluorine adsorbed therein at a temperature and for a time sufficient to form fluorinated alkanes wherein the alkene is not perhalogenated at the double-bonded carbons.

Other advantages of the present invention will become apparent from the following description and appended claims.

DETAILED DESCRIPTION OF THE PREFERRED EMBODIMENTS

Elemental fluorine is deactivated by adsorption on a carbon surface. Examples of preferred carbon surfaces include carbon black activated carbon, and carbon sieves. The most preferred carbon surface is activated carbon. Commercially available elemental fluorine, carbon black, activated carbon, and carbon sieves may be used in practicing the present process and are adequate for sufficient fluorine adsorption for reaction with the alkene. Preferably, the carbon is in pellet form and has a size of about 400 mesh to 5 mm.

Adsorption of the elemental fluorine on the carbon surface may be conducted at room temperature. The $F_2$ is preferably diluted with an inert gas such as nitrogen, helium, argon, or the like. The concentration of $F_2$ in the inert gas is preferably about 5 to about 40 vol %. The flow rates of the gases are adjusted accordingly in order to obtain the desired $F_2$ concentration.

The carbon should adsorb as much fluorine as possible. The carbon should adsorb greater than 10% by weight fluorine. To practice the absorption step, the gases may simply be passed through the carbon source.

As the mixture of elemental fluorine and inert gas passes through the carbon surface, the temperature of the carbon surface increases because the fluorine adsorption reaction is exothermic. The temperature of the carbon surface should be maintained below about 150° C. so that extensive amounts of adsorbed $F_2$ will not form covalent bonds with carbon; covalent carbon fluorine bonds are unreactive toward alkenes and are not useful in the present process. Cooling of the carbon surface may be desirable during elemental fluorine adsorption to preserve a large portion of the adsorbed fluorine in a reactive state; a cooling jacket may be used for this purpose.

It is believed that the elemental fluorine may be adsorbed on the carbon surface simultaneously with the reaction of the alkene. Preferably, the elemental fluorine is adsorbed on the carbon surface before reaction with an alkene.

It is believed that most alkenes may be fluorinated by the present process. Based on the failure of perchloroethylene to react to form fluorinated alkanes as taught by the aforementioned Watanabe et al article, it is believed that alkenes which are perhalogenated at the double-bonded carbons will not form fluorinated alkanes in the present process. As such, these alkenes are not considered useful in the present process. Preferably, an alkene having 2 to 6 carbon atoms is used. Examples of alkenes having 2 to 6 carbon atoms include ethylene; propane; 1-butene; 2-butene; 1-pentene; 2-pentene; 1-hexene; 2-hexene; 3-hexene; vinylidene chloride; vinylidene fluoride; 1-bromo-1-propene; 2-bromopropene; 2-chloropropene; 1,1-dichloropropene; 2-bromo-2-butene; and 2-chloro-2-butene. These alkenes are available commercially. The most preferred alkenes are ethylene and vinylidene fluoride.

Preferably, the alkene is diluted with an inert gas such as nitrogen before fluorination. Dilution helps to control the reaction temperature. If an inert gas is to be used, about 90 to about 20% of the total gases may be inert gas.

The reaction may be conducted over a wide temperature range. Generally, a temperature range of about 25° to about 200° C. may be employed although the reaction may be conducted below 25° C. or above 200° C. with a resulting lower conversion and selectivity. Preferably, the reaction is conducted at a temperature of about 50° to about 150° C. The contact time should be at least one second.

When the alkene used is the preferred ethylene, the major product is 1,1,1,2-tetrafluoroethane if residual elemental fluorine is present in the reactor. The term "residual fluorine" means that after the fluorine adsorption step and before the alkene feed step, the reactor was not purged so as to remove residual fluorine therein.

When the alkene used is the preferred ethylene and residual fluorine is not present, the major product is 1,2-difluoroethane. As such, it is believed that fluorine adds to the double bond. Although not wishing to be bound by theory, it is believed that the energetics of the elemental fluorine are moderated by adsorption on the carbon surface. As such, the reaction mechanism between the fluorine and alkene is altered. Degradation of the ethylene does not occur because no single carbon atom product forms.

When the alkene used is the preferred vinylidene fluoride, the major products are 1,1,1-trifluoroethane and 1,1,1,2-tetrafluoroethane. It is believed that 1,1,1-trifluoroethane is formed from the addition of HF to the double bond while 1,1,1,2-tetrafluoroethane is formed from the addition of $F_2$ to the double bond possible HF sources are as follows. HF may be generated from the reaction of $F_2$ with moisture or hydroxy groups present on the carbon surface; HF may also escape from the HF-scrubber and be absorbed on the carbon surface with fluorine.

The fluorinated alkanes produced by the present process may be used as blowing agents and solvents. A fluorinated alkane such as R134a is particularly useful as a refrigerant.

The present invention is more fully illustrated by the following non-limiting Examples.

EXAMPLE 1

Examples 1–5 are directed to the preparation of fluorinated alkanes wherein the alkene used is ethylene.

Part A—

In a typical run, 40–45 grams of Calgon BPL activated carbon (4×10 mesh size) were packed in an 18 inch (46 cm) long and ¾ inch (1.9 cm) diameter Monel pipe. Elemental fluorine diluted with nitrogen was passed through the pipe. The flow rate of fluorine was approximately 15 cc/min; the flow rate of nitrogen was about 127 cc/min. A heat band was noticed as soon as the fluorine reached the activated carbon bed. The temperature of this heat band was about 100° C. As the heat band disappeared at the top of the reactor, the adsorption of fluorine was completed. The activated carbon then contained 36 wt % fluorine. It possessed 9 wt % of free oxidizing power meaning that 9 wt % of the $F_2$/carbon adduct can oxidize KI to iodine in alcohol/water solution. As those skilled in the art know, this is a standard method for determining the reactivity of $F_2$.

Part B—

Upon completion of $F_2$-adsorption as indicated in Part A the fluorine feed was terminated. Ethylene diluted with nitrogen was subsequently fed to the $F_2$-adsorbed carbon bed at 50° C. The flow rate of ethylene was about 4 cc/min; the nitrogen was about 50 cc/min. The effluent gas mixture was passed through a cold trap at −80° C. The reaction continued for 4.5 hours and the products were collected in the same cold trap. The contents of the cold trap were analyzed using a GC-Mass Spectrometer. The product compositions are listed under Example 1 in Table 1 below.

TABLE 1

| | EXAMPLES | | | | |
|---|---|---|---|---|---|
| | 1 | 2 | 3 | 4 | 5 |
| Temp. (°C.) | 50 | 50 | 70 | 150 | 200 |
| $CFH_2CH_3$ | 3.5 | 15 | 0.3 | 11 | 12 |
| $CHF_2CH_3$ | 9.4 | 23 | 1.7 | 0.2 | — |
| $CH_2FCH_2F$ | 37 | 50 | 97 | 86 | 54 |
| $CHF_2CH_2F$ | 3.7 | 13 | 0.8 | 0.4 | 6.1 |
| $CFH_2CF_3$ | 45 | — | — | 2.4 | — |
| 4-Carbon Compounds | — | — | — | — | 28 |

It is believed that residual free fluorine must have been left in the reactor during the running of Example 1 in order for 1,1,1,2-tetrafluoroethane to form. As such, 1,1,1,2-tetrafluoroethane may be produced as a major product by using this process if a small quantity of free fluorine is fed to the carbon surface continuously during the fluorination of ethylene.

Although a GC-mass spectrometer was used to analyze the product alkanes, the product alkanes may be readily separated by distillation due to boiling point differences. For example, the products of Example 1 have the boiling points listed in Table 2 below.

TABLE 2

| PRODUCT | BOILING POINT (°C.) |
|---|---|
| $CFH_2CH_3$ | −37.7 |
| $CHF_2CH_3$ | −24.7 |
| $CH_2FCH_2F$ | +30.7 |
| $CFH_2CF_3$ | −26.5 |

EXAMPLE 2

After completing the procedure of Part A of Example 1, the reactor was purged with nitrogen for at least 0.5 hour after the completion of $F_2$-adsorption. Ethylene was then fed to the reactor at a flow rate and concentration similar to those indicated in Part B of Example 1. The product compositions for a 5 hour reaction are listed under Example 2 of Table 1 above.

The major product was 1,2-difluoroethane while the remaining products were monofluoroethane; 1,1-difluoroethane; and 1,1,2-trifluoroethane.

EXAMPLES 3–5

The same procedure and similar conditions as in Example 1 were employed except the reaction temperature was raised to 70°, 150°, and 200° C. respectively in three separate runs. The products were analyzed using a GC-Mass spectrometer. The results are listed under Examples 3, 4, and 5 respectively in Table 1 above.

At 70° C., the selectivity of producing 1,2-difluoroethane was 97% with an ethylene conversion of 30%. Comparable to the reaction in Example 2, the remaining products were monofluoroethane; 1,1-difluoroethane; and 1,1,2-trifluoroethane.

At 150° C., the selectivity of producing 1,2-difluoroethane was 86%. The remaining products were monofluoroethane; 1,1-difluoroethane; 1,1,2-trifluoroethane; and 1,1,1,2-tetrafluoroethane.

At 200° C., partially fluorinated products with four carbons started to appear; this suggests that the coupling reaction occurs at this temperature.

EXAMPLES 6–9

Examples 6–9 are directed to the preparation of fluorinated alkanes wherein the alkene used is vinylidene fluoride.

The procedure and conditions as in Example 1 were employed, except vinylidene fluoride was used instead of ethylene. The vinylidene fluoride was fed to the reactor at approximately 8 cc/min and it was diluted with nitrogen before reaching the reactor. The flow rate of nitrogen was about 50 cc/min. The reaction temperatures for 4 different runs were 50°, 100°, 150°, and 200° C. The products were collected in the cold trap at −80° C. separately. The product compositions for each different run were determined using a GC-Mass spectrometer and are listed under Examples 6, 7, 8, and 9 respectively in Table 3 below.

TABLE 3

| | EXAMPLES | | | |
|---|---|---|---|---|
| | 6 | 7 | 8 | 9 |
| Temp. (°C.) | 50 | 100 | 150 | 200 |
| $CF_3CH_3$ | 82 | 58 | 16 | 5.5 |
| $CF_3CH_2F$ | 18 | 28 | 6.8 | 1.7 |
| $C_3H_2F_6$ | — | 1 | 0.3 | 0.4 |
| $C_4H_4F_6$ | — | 11 | 71 | 32 |
| $CF_3CF(CF_3)CF_2CF_3$ | — | — | — | 25 |
| Unknowns | — | — | 6.2 | 35 |

At 50° C., the major product was 1,1,1-trifluoroethane while the remaining product was 1,1,1,2-tetrafluoroethane.

At 100° C., the major product was 1,1,1-trifluoroethane. The remaining products were 1,1,1,2-tetratluoroethane hexafluoropropane ($C_3H_2F_6$), and hexafluorobutane ($C_4H_4F_6$). It should be noted that the specific types of isomers of hexafluoropropane and hexafluorobutane were not determined.

At 150° C., the major product was hexafluorobutane. Although not wishing to be bound by theory, it is believed that the hexafluorobutane was formed by the coupling reaction between two molecules of vinylidene fluoride which was followed by fluorination thereof. The remaining products were 1,1,1-trifluoroethane; 1,1,1,2-tetrafluoroethane; hexafluoropropane; and unknowns. The unknowns consist of small quantities of many different fluorinated species.

At 200° C., perfluoroisopentane began to appear. The mechanism of forming perfluoroisopentane is unknown. The other products were 1,1,1-trifluoroethane; 1,1,1,2-tetrafluoroethane; hexafluoropropane; hexafluorobutane; and unknowns.

Although a GC-mass spectrometer was used to analyze the product alkanes, the product alkanes may be readily separated by distillation due to boiling point differences. For example, the products of Example 7 have the boiling points listed in Table 4 below.

TABLE 4

| PRODUCT | BOILING POINT (°C.) |
|---|---|
| $CF_3CH_3$ | −47.3 |
| $CF_3CH_2F$ | −26.5 |

EXAMPLES 10–24

After completion of the procedure of Part A of Example 1, the reactor is purged with nitrogen for at least 0.5 hour. In each of the Examples listed in Table 5 below, the alkene diluted with nitrogen is subsequently fed to the F$_2$-adsorbed carbon bed at the temperature indicated in Table 5 below. The flow rate of alkene is about 4 cc/min while the flow rate of nitrogen is about 50 cc/min. The reaction temperature is about 50° to about 150° C. The effluent gas mixture is passed through a cold trap at −80° C. The products are collected in the same cold trap and analyzed using a GC-mass spectrometer.

TABLE 5

| EX. | ALKENE |
|---|---|
| 10 | Propene |
| 11 | 1-butene |
| 12 | 2-butene |
| 13 | 1-pentene |
| 14 | 2-pentene |
| 15 | 1-hexene |
| 16 | 2-hexene |
| 17 | 3-hexene |
| 18 | vinylidene chloride |
| 19 | 1-bromo-1-propene |
| 20 | 2-bromopropene |
| 21 | 2-chloropropene |
| 22 | 1,1-dichloropropene |
| 23 | 2-bromo-2-butene |
| 24 | 2-chloro-2-butene |

Having described the invention in detail and by reference to preferred embodiments thereof, it will be apparent that modifications and variations are possible without departing from the scope of the invention defined in the appended claims.

What is claimed is:

1. A process comprising the steps of:
reacting a member selected from the group consisting of ethylene, propene, 1-butene, 2-butene, 1-pentene, 2-pentene, 1-hexene, 2-hexene, 3-hexene, vinylidene chloride, vinylidene fluoride, 1-bromo-1-propene, 2-bromopropene, 2-chloropropene, 1,1-dichloropropene, 2-bromo-2-butene, and 2-chloro-2-butene with carbon having elemental fluorine adsorbed therein at a temperature of about 25° C. to about 200° C. for a time sufficient to form fluorinated alkanes having the same number of carbon atoms as said member.

2. The process of claim 1 wherein said carbon is carbon sieve.

3. The process of claim 1 wherein said carbon is carbon black.

4. The process of claim 1 wherein said carbon is activated carbon.

5. The process of claim 1 wherein before said reaction, said fluorine is adsorbed into said carbon.

6. The process of claim 1 wherein said member is vinylidene fluoride.

7. The process of claim 1 wherein said member is ethylene.

8. The process of claim 1 wherein said process is conducted at a temperature of about 50° to about 150° C.

9. The process of claim 1 wherein said carbon has greater than 10% by weight said fluorine adsorbed therein.

10. The process of claim 7 wherein said reaction occurs in the presence of residual fluorine.

11. The process of claim 1 wherein said member is propene.

12. The process of claim 1 wherein said member is diluted with inert gas before said reaction.

13. The process of claim 7 wherein said process is conducted at a temperature of about 70° to about 150° C.

14. The process of claim 6 wherein said process is conducted at a temperature of about 50° to about 100° C.

* * * * *